United States Patent
Ousdigian

(10) Patent No.: US 7,930,024 B2
(45) Date of Patent: Apr. 19, 2011

(54) REDUCING INAPPROPRIATE DELIVERY OF THERAPY FOR SUSPECTED NON-LETHAL ARRHYTHMIAS

(75) Inventor: Kevin T. Ousdigian, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 824 days.

(21) Appl. No.: 10/755,185

(22) Filed: Jan. 8, 2004

(65) Prior Publication Data

US 2005/0154421 A1    Jul. 14, 2005

(51) Int. Cl.
*A61N 1/365* (2006.01)
*A61B 5/0464* (2006.01)

(52) U.S. Cl. .................. 607/5; 607/4; 600/518

(58) Field of Classification Search .............. 607/4, 5; 600/515–518
See application file for complete search history.

(56) References Cited

U.S. PATENT DOCUMENTS

| | | |
|---|---|---|
| 4,860,749 A | 8/1989 | Lehmann |
| 5,226,415 A | 7/1993 | Girodo et al. |
| 5,257,621 A | 11/1993 | Bardy et al. ............ 607/5 |
| 5,312,441 A | 5/1994 | Mader et al. |
| 5,411,530 A | 5/1995 | Akhtar |
| 5,462,060 A | 10/1995 | Jacobson et al. |
| 5,564,434 A | 10/1996 | Halperin et al. |
| 5,730,141 A | 3/1998 | Fain et al. |
| 5,868,793 A | 2/1999 | Nitzsche et al. |
| 5,891,170 A | 4/1999 | Nitzsche et al. |
| 6,061,592 A * | 5/2000 | Nigam .................... 600/518 |
| 6,169,923 B1 | 1/2001 | Kroll |
| 6,317,632 B1 | 11/2001 | Krig et al. |
| 6,487,443 B2 * | 11/2002 | Olson et al. ............. 600/518 |
| 2002/0188215 A1 | 12/2002 | Ferek-Petric ........... 600/518 |
| 2003/0074026 A1 | 4/2003 | Thompson et al. |
| 2003/0204215 A1 | 10/2003 | Gunderson et al. |

OTHER PUBLICATIONS

U.S. Appl. No. 10/135,080, filed Apr. 29, 2002 Method and Apparatus for Identifying Cardiac and Non-Cardiac Oversensing Using Intracardiac Electrograms.

* cited by examiner

*Primary Examiner* — Carl H. Layno
*Assistant Examiner* — Tammie K Heller
(74) *Attorney, Agent, or Firm* — Michael J. Ostrom; Stephen W. Baver

(57) ABSTRACT

An implantable medical device (IMD) identifies suspected non-lethal ventricular arrhythmia, and takes one or more actions in response to the identification to avoid or delay delivery of a defibrillation or cardioversion shock. The IMD employs number of intervals to detect (NID) thresholds for detection of ventricular arrhythmias. When a NID threshold is met, the IMD determines whether the ventricular rhythm is a suspected non-lethal rhythm despite satisfying a NID threshold. In some embodiments, the IMD increases the NID threshold, i.e., extends the time for detection, in response to identifying a rhythm as a suspected non-lethal rhythm, and monitors subsequent ventricular beats to determine if the increased NID threshold is met before detecting a ventricular arrhythmia and delivering therapy. The IMD can determine whether a rhythm is a suspected non-lethal arrhythmia by, for example, comparing the median ventricular cycle length (VCL) to the median atrial cycle length (ACL).

51 Claims, 10 Drawing Sheets

US 7,930,024 B2

REDUCING INAPPROPRIATE DELIVERY OF THERAPY FOR SUSPECTED NON-LETHAL ARRHYTHMIAS

TECHNICAL FIELD

The invention relates to cardiac pacing, and more particularly, to detection and treatment of ventricular arrhythmias.

BACKGROUND

Implantable medical devices (IMDs), such as implantable pacemakers, utilize a variety of techniques and/or algorithms to detect heart arrhythmias. Ventricular arrhythmias, such as ventricular fibrillation (VF) and ventricular tachycardia (VT), are particularly dangerous, and can result in death if not quickly terminated by delivery of a therapy. Consequently, IMDs are programmed to deliver therapy, such as defibrillation or cardioversion shocks, upon detecting VF or VT.

IMDs typically detect VF and VT by measuring the intervals between ventricular depolarizations, i.e., ventricular cycle lengths (VCLs), and determining whether recently measured VCLs are indicative of VF or VT. However, supraventricular tachycardias (SVTs), such as sinus tachycardia, atrial fibrillation, atrial flutter, and reentrant atrial tachycardia, can be conducted to the ventricles, and can lead to short VCLs that falsely indicate VF or VT. Delivery of defibrillation or cardioversion shocks to the ventricles in situations where an SVT causes VF or VT to be falsely detected is generally not clinically needed and usually is ineffective in terminating the SVT. Moreover, defibrillation and cardioversion shocks, which can be delivered a number of times during an SVT episode that leads to false VF of VT detection, can cause significant patient discomfort or induce a VF or VT.

In order to avoid false detection of VF or VT during SVT episodes, some IMDs apply further analysis the ventricular rhythm and additionally analyze the atrial rhythm to determine if an SVT is the cause of the fast ventricular rhythm, i.e., apply specific SVT detection rules. If the criteria for VF or VT is met during a particular ventricular interval and the further analysis indicates the presence of an SVT, an IMD typically avoids detection of VF or VT during that interval and, in some cases, delivers a therapy to one or more atria, such as anti-tachycardia pacing or a cardioversion shock. Nonetheless, because IMDs are programmed to err on the side of over-detecting potentially lethal VF and VT, IMDs occasionally inappropriately detect VF or VT when the fast ventricular rhythm is non-lethal, e.g., caused by an SVT, despite such additional analysis.

In order to avoid inappropriate delivery of defibrillation and cardioversion shocks, and the substantial patient discomfort associated therewith, clinicians in some cases program IMDs to prevent delivery of therapy for ventricular rhythms that are slower than a certain median of mean cycle length. This makeshift solution is not without problems, however. Slow arrhythmias can cause patient symptoms, such as fatigue, dizziness, and fainting, and can quickly accelerate into a more dangerous arrhythmia. Further, such clinician programming generally does not eliminate all inappropriate detection of VF and VT.

SUMMARY

In general, the invention is directed to techniques for reducing inappropriate delivery of therapy to treat non-lethal ventricular arrhythmias, e.g., ventricular arrhythmias caused by a supraventricular tachycardia (SVT). An implantable medical device (IMD), such as a pacemaker or pacemaker-cardiovertor-defibrillator (PCD), identifies a suspected non-lethal ventricular arrhythmia, and takes one or more actions in response to the identification to avoid or delay delivery of a defibrillation or cardioversion shock. By reducing inappropriate delivery of therapy in this manner, the IMD can reduce the unnecessary occurrences of patient discomfort associated with delivery of such therapy.

The IMD employs number of intervals to detect (NID) thresholds for detection of ventricular arrhythmias. When a NID is met, the IMD determines whether the ventricular rhythm is a suspected non-lethal rhythm despite satisfying the NID. In some embodiments, the IMD increases the NID, i.e., extends the time for detection, in response to identifying a rhythm as a suspected non-lethal rhythm, and monitors subsequent ventricular beats to determine whether the increased NID is met before detecting a ventricular arrhythmia and delivering therapy. By increasing the NID, the IMD allows more time for an SVT to terminate or the ventricular cycle length to slow down, for evidence of the SVT to become apparent, or for a slow ventricular arrhythmia to spontaneously terminate or develop into a ventricular arrhythmia that warrants delivery of a therapeutic shock.

In some embodiments, the IMD additionally or alternatively changes the therapy to be delivered in response to determining that a rhythm is a suspected non-lethal arrhythmia. For example, where a sequence of defibrillation or cardioversion shocks was scheduled to be delivered in response to detection of a ventricular fibrillation (VF) or ventricular tachycardia (VT), the IMD can reduce the number of shocks in the sequence and/or deliver anti-tachycardia pacing (ATP) instead of or prior to delivery of the defibrillation or cardioversion shocks. Where ATP was scheduled, the IMD can reduce or increase the number of ATP attempts. The changed therapy can be delivered upon the determination that the rhythm is suspected non-lethal, or, where NID-increasing is additionally implemented, upon a determination that an increased NID has been met.

The IMD can determine whether a rhythm is a suspected non-lethal arrhythmia in a number of ways. For example, in some embodiments, the IMD compares the median ventricular cycle length (VCL) to the median atrial cycle length (ACL), and makes the determination based on the comparison. A median VCL that is longer than the median ACL, or shorter than the median ACL by less than a threshold value is indicative of the presence of an SVT that may be causing the fast ventricular rhythm. In some embodiments, mean ventricular and atrial cycle lengths are used instead of median ventricular and atrial cycle lengths.

In some embodiments, the IMD uses other indicators instead of or in addition to a comparison of ventricular and atrial cycle lengths to determine whether a rhythm is a suspected non-lethal arrhythmia. For example, the IMD can determine whether a rhythm is a suspected non-lethal arrhythmia based on the regularity of ventricular cycle lengths and/or morphological features of the rhythm, A:V association, rate of onset within measured ACLs, VCLs, or A-V intervals, or some physiological parameter of the patient such as an intracardiac pressure, respiration rate, respiration depth, or activity level. In some embodiments, the IMD employs a minimum median or mean VCL for suspected non-lethal arrhythmias. In other words, arrhythmias less than a threshold median or mean VCL will be will be presumed to be dangerous and accordingly will be detected and treated.

In some embodiments, the IMD further determines whether a suspected non-lethal arrhythmia is a slow suspected non-lethal arrhythmia by determining whether the median or mean VCL is greater than or equal to a slow suspected non-lethal threshold. In such embodiments, the IMD can treat slow suspected non-lethal arrhythmias differently than other suspected non-lethal arrhythmias because they are presumed to pose less of a risk to the patient. In particular, the IMD can increase the NID threshold by a greater amount for slow suspected rhythms than other suspected rhythms and/or provide a different therapy change for slow suspected rhythms than other suspected rhythms. For example, where the IMD would reduce the number of defibrillation or cardioversion shocks and add ATP attempts for suspected non-lethal arrhythmias, the IMD can eliminate the shocks and instead deliver ATP alone for slow suspected non-lethal arrhythmias. In some embodiments, the IMD can simply not deliver any therapy upon detection of a slow suspected non-lethal arrhythmia.

In some embodiments, the IMD classifies relatively slow, monomorphic VTs as suspected non-lethal arrhythmias instead of or in addition to classifying suspected SVTs as suspected non-lethal arrhythmias. Slower monomorphic VTs are often terminable by ATP or spontaneously terminate, and consequently, like SVTs, do not pose as great a risk to the patient as less stable or faster VTs or VF. Monomorphic VTs are classified as suspected non-lethal arrhythmias based on the regularity of measured VCL and/or morphological features of the ventricular rhythm, as well as the absolute value of the VCL. In such embodiments, the IMD can employ a minimum median or mean VCL for suspected non-lethal arrhythmias, and can further classify suspected non-lethal arrhythmias as slow suspected non-lethal arrhythmias, as described above.

In some embodiments, the IMD additionally or alternatively determines whether the NID threshold for a ventricular arrhythmia has been met in error due to cardiac or non-cardiac oversensing. Cardiac oversensing can for example be caused by T-wave oversensing, while non-cardiac oversensing is caused by noise within a detected cardiac signal, such as noise caused by lead failure, a loose set screw, or the like. When the IMD identifies cardiac or non-cardiac oversensing, the IMD classifies the ventricular rhythm as a suspected non-lethal cardiac rhythm, and can increase the NID threshold and/or modify a scheduled therapy as described above. Cardiac and non-cardiac oversensing can result in very short measured VCLs, and the IMD can identify cardiac and non-cardiac oversensing by determining that a median or mean VCL is less than or equal to an oversensing threshold value.

In one embodiment, the invention is directed to a method in which ventricular cycle lengths within a ventricular rhythm are measured, and it is determined that a number of intervals to detect (NID) threshold for a ventricular arrhythmia is met based on the measured ventricular cycle lengths. It is further determined that the ventricular rhythm is a suspected non-lethal arrhythmia subsequent to the determination that the NID threshold is met, and the NID threshold is increased based on the determination that the rhythm is a suspected non-lethal arrhythmia. Subsequent ventricular cycle lengths are measured to determine whether the increased NID threshold is met.

In another embodiment, the invention is directed to a medical device that includes electrodes to detect depolarizations of ventricles of a heart, a memory to store a number of intervals to detect threshold for a ventricular arrhythmia, and a processor. The processor measures ventricular cycle lengths within a ventricular rhythm based on detected ventricular depolarizations, determines that the NID threshold is met based on the measured ventricular cycle lengths, determines that the ventricular rhythm is a suspected non-lethal arrhythmia subsequent to the determination that the NID is met, increases the NID based on the determination that the rhythm is a suspected non-lethal arrhythmia, and measures subsequent ventricular cycle lengths based on detected ventricular depolarizations to determine whether the increased NID is met.

In another embodiment, the invention is directed to a medical device comprising means for detecting depolarizations of ventricles of a heart, means for measuring ventricular cycle lengths within a ventricular rhythm based on detected ventricular depolarizations, means for determining that the NID threshold is met based on the measured ventricular cycle lengths, means for determining that the ventricular rhythm is a suspected non-lethal arrhythmia subsequent to the determination that the NID is met, means for increasing the NID based on the determination that the rhythm is a suspected non-lethal arrhythmia, and means for measuring subsequent ventricular cycle lengths based on detected ventricular depolarizations to determine whether the increased NID is met In another embodiment, the invention is directed to a method in which ventricular cycle lengths within a ventricular rhythm are measured, and it is determined that a number of intervals to detect (NID) threshold for a ventricular arrhythmia is met based on the measured ventricular cycle lengths. It is further determined that the ventricular rhythm is a suspected non-lethal arrhythmia subsequent to the determination that the NID is met, and a therapy scheduled for the ventricular arrhythmia is changed based on the determination the that ventricular rhythm is a suspected non-lethal arrhythmia.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
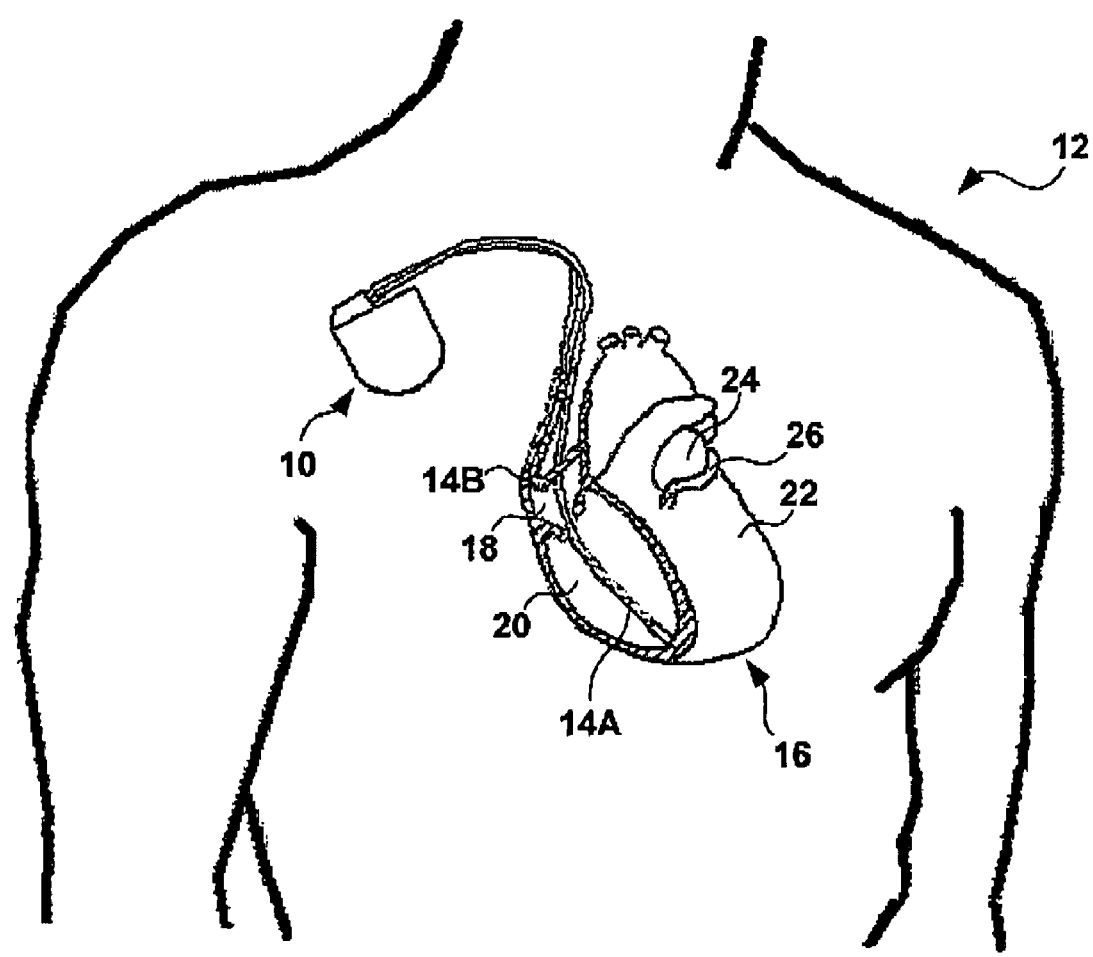
FIG. 1 is a conceptual diagram illustrating an example implanted medical device that reduces inappropriate delivery of therapy for suspected non-lethal arrhythmias implanted within a patient.

FIG. 1 is a conceptual diagram illustrating an example implanted medical device (IMD) 10 that reduces inappropriate delivery of therapy for suspected non-lethal arrhythmias implanted within a patient 12. In exemplary embodiments, IMD 10 takes the form of a multi-chamber pacemaker with cardioversion and/or defibrillation capability. In the exemplary embodiment illustrated in FIG. 1, IMD 10 is coupled to leads 14A and 14B (collectively "leads 14") that extend into the heart 16 of patient 12. More particularly, right ventricular (RV) lead 14A extends through one or more veins (not shown), the superior vena cava, and right atrium 18, and into right ventricle 20, and right atrial (RA) lead 14A extends through the veins and superior vena cava, and into the right atrium 18 of heart 16.

IMD 10 senses electrical signals attendant to the depolarization and repolarization of heart 16 and provides pacing pulses via electrodes (not shown) located on leads 14. The electrodes located on leads 14 are unipolar or bipolar. In some embodiments, leads 14 include coil defibrillation electrodes, and IMD 10 also provides defibrillation and/or cardioversion shocks via the defibrillation electrodes.

IMD 10 detects ventricular arrhythmias via the electrodes located on leads 14. IMD 10 measures ventricular cycle lengths (VCLs) via the electrodes located on leads 14, and detects ventricular arrhythmias, such as ventricular fibrillation (VF), ventricular tachycardia (VT) and fast VT (FVT), based on the measured VCLs. In exemplary embodiments, IMD 10 specifies a VCL zone for each of the ventricular arrhythmia types, and determines whether measured VCLs fall into the specified zones.

IMD 10 detects a ventricular arrhythmia if a sufficient number of VCLs measured during a time period that precedes and includes the current ventricular interval fall within the VCL zone associated with that arrhythmia. IMD 10 stores a number of intervals to detect (NID) threshold for each arrhythmia that identifies the required number of VCLs for detection of an arrhythmia within each zone. The NID threshold is conventionally referred to in shorthand form as "the NID." The NID can be expressed, for example, as a number of intervals within the zone within a period of time, i.e., a "time to detect," a number of consecutive intervals within the zone, or as a fraction, e.g., "A" of the last "B" intervals within the zone.

As will be described in greater detail below, when IMD 10 determines that a NID for a ventricular arrhythmia is met, IMD 10 further determines whether the ventricular rhythm in question is a suspected non-lethal arrhythmia, e.g., a supraventricular tachycardia (SVT) or slower monomorphic VT. If the ventricular rhythm is a suspected non-lethal arrhythmia, IMD 10 takes one or more actions to reduce the likelihood of inappropriate delivery of therapy. In some embodiments, for example, IMD 10 increases the NID for the initially detected arrhythmia, and measures subsequent VCLs to determine if the increased NID is met. In some embodiments, IMD 10 changes a ventricular therapy scheduled for the initially detected arrhythmia. In some embodiments, IMD 10 both increases the NID and changes the therapy. In some embodiments, IMD 10 additionally provides an atrial therapy, such as atrial anti-tachycardia pacing (ATP) in response to the determination that the ventricular rhythm is a suspected non-lethal ventricular arrhythmia.

Changing a ventricular therapy can include canceling some or all of the scheduled therapies for the initially detected arrhythmia, e.g., canceling defibrillation or cardioversion shocks or canceling both shocks and scheduled anti-tachycardia pacing (ATP) attempts. Changing a ventricular therapy can also include adding ATP attempts where none are scheduled, or increasing or decreasing the number of schedule ATP attempts. In some embodiments, changing a ventricular therapy includes changing a shock energy level or pathway to increase the likelihood of terminating an underlying SVT.

The configuration of IMD 10 and leads 14 illustrated in FIG. 1 is merely exemplary. In various embodiments, IMD 10 is coupled any number of leads 14 that extend to a variety of positions within or outside of heart 16. For example, in some embodiments, IMD 10 is coupled to a lead 14 that extends to a position within coronary sinus and great vein 26 near left ventricle 24 for left ventricular sensing and/or pacing. In some embodiments, at least some of leads 14 are epicardial leads. Further, in some embodiments, IMD 10 is not implanted within patient 12, but is instead coupled with percutaneous leads 14 that extend through the skin of patient 12 to a variety of positions within or outside of heart 16, or transcutaneous leads that detect electrical activity within the heart from positions on the surface, e.g., skin, of patient.

Figure 2:
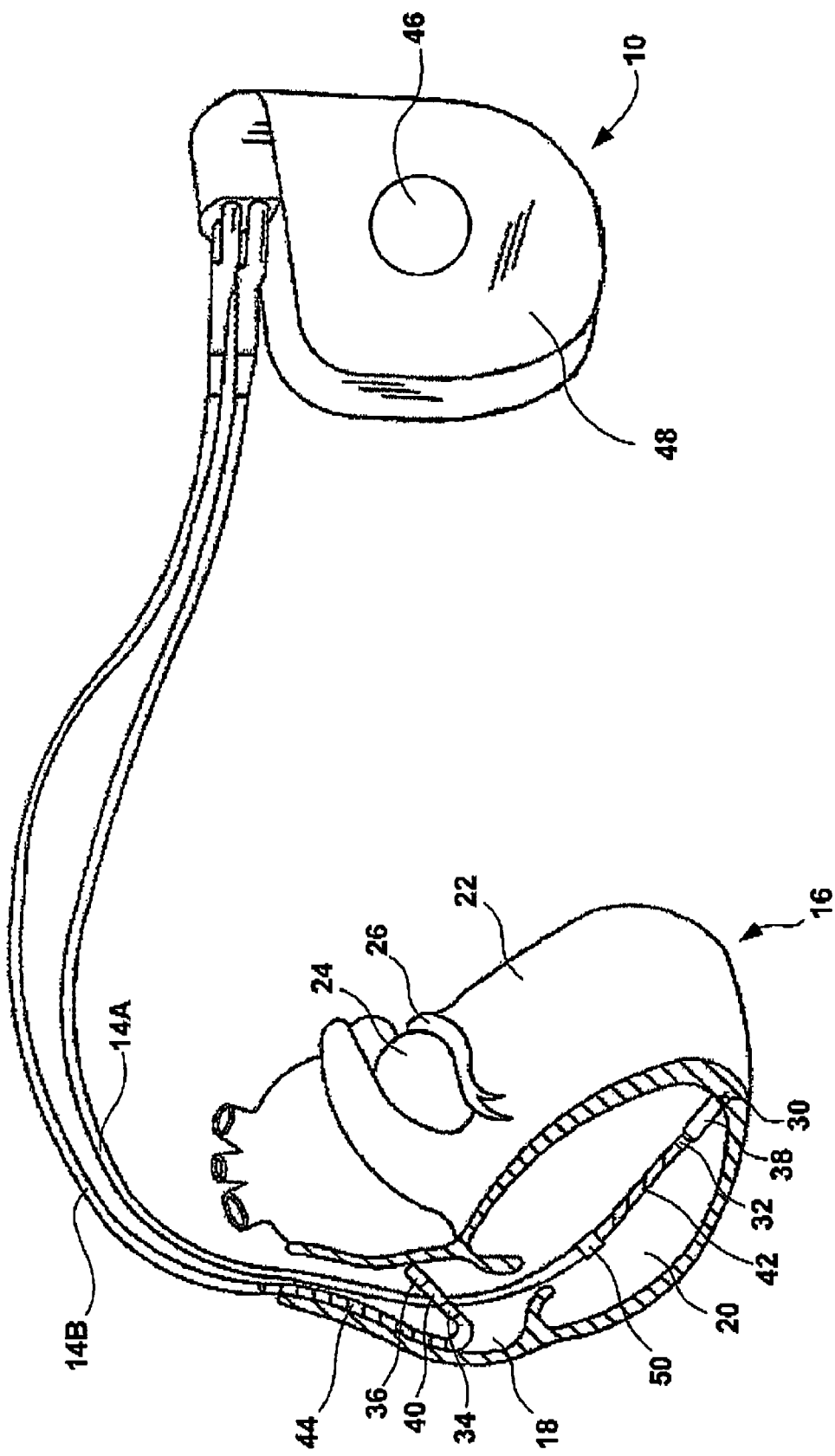
FIG. 2 is a conceptual diagram illustrating the implantable medical device of FIG. 1 and the heart of the patient in greater detail.

FIG. 2 is conceptual diagram further illustrating IMD 10 and heart 16 of patient 12. In exemplary embodiments, each of leads 14 includes an elongated insulative lead body carrying a number of concentric coiled conductors separated from one another by tubular insulative sheaths. Located adjacent distal end of leads 14A and 14B are bipolar electrodes 30 and 32, and 34 and 36, respectively. In exemplary embodiments, electrodes 30 and 34 take the form of ring electrodes, and electrodes 32 and 36 take the form of extendable helix tip electrodes mounted retractably within insulative electrode heads 38 and 40, respectively. Each of the electrodes 30-36 is coupled to one of the coiled conductors within the lead body of its associated lead 14.

Sense/pace electrodes 30-36 sense electrical signals attendant to the depolarization and repolarization of heart 16. The electrical signals are conducted to IMD 10 via leads 14. In exemplary embodiments, at least some of sense/pace electrodes 30-36 further deliver pacing to cause depolarization of cardiac tissue in the vicinity thereof. In some embodiments, IMD 10 also includes one or more indifferent housing electrodes, such as housing electrode 46, formed integrally with an outer surface of the hermetically sealed housing 48 of IMD 10. In such embodiments, any of electrodes 30-36 are capable of being used for unipolar sensing or pacing in combination with housing electrode 46.

As shown in FIG. 2, leads 14A and 14B also carry elongated coil defibrillation electrodes 42 and 44, respectively. In exemplary embodiments, defibrillation electrodes 42 and 44 are fabricated from platinum, platinum alloy or other materials known to be usable in implantable defibrillation electrodes, and may be about 5 cm in length. IMD 10 delivers cardioversion and/or defibrillation therapy to heart 16, and more particularly right ventricle 20 and left ventricle 22, via one or more of elongated coil electrodes 42 and 44.

In some embodiments, IMD 10 also includes a sensor 50 that generates a signal as a function of a physiological parameter of patient 12. In such embodiments, IMD 10 processes the output of sensor 50 to determine whether a ventricular rhythm initially detected as a ventricular arrhythmia is a suspected non-lethal ventricular arrhythmia. In exemplary embodiments, sensor 50 takes the form of an intracardiac pressure sensor such as a capacitive absolute pressure sensor, as described in U.S. Pat. No. 5,564,434 to Halperin, et al., hereby incorporated by reference herein in its entirety, a piezoelectric crystal, or piezoresistive pressure transducer.

Figure 3:
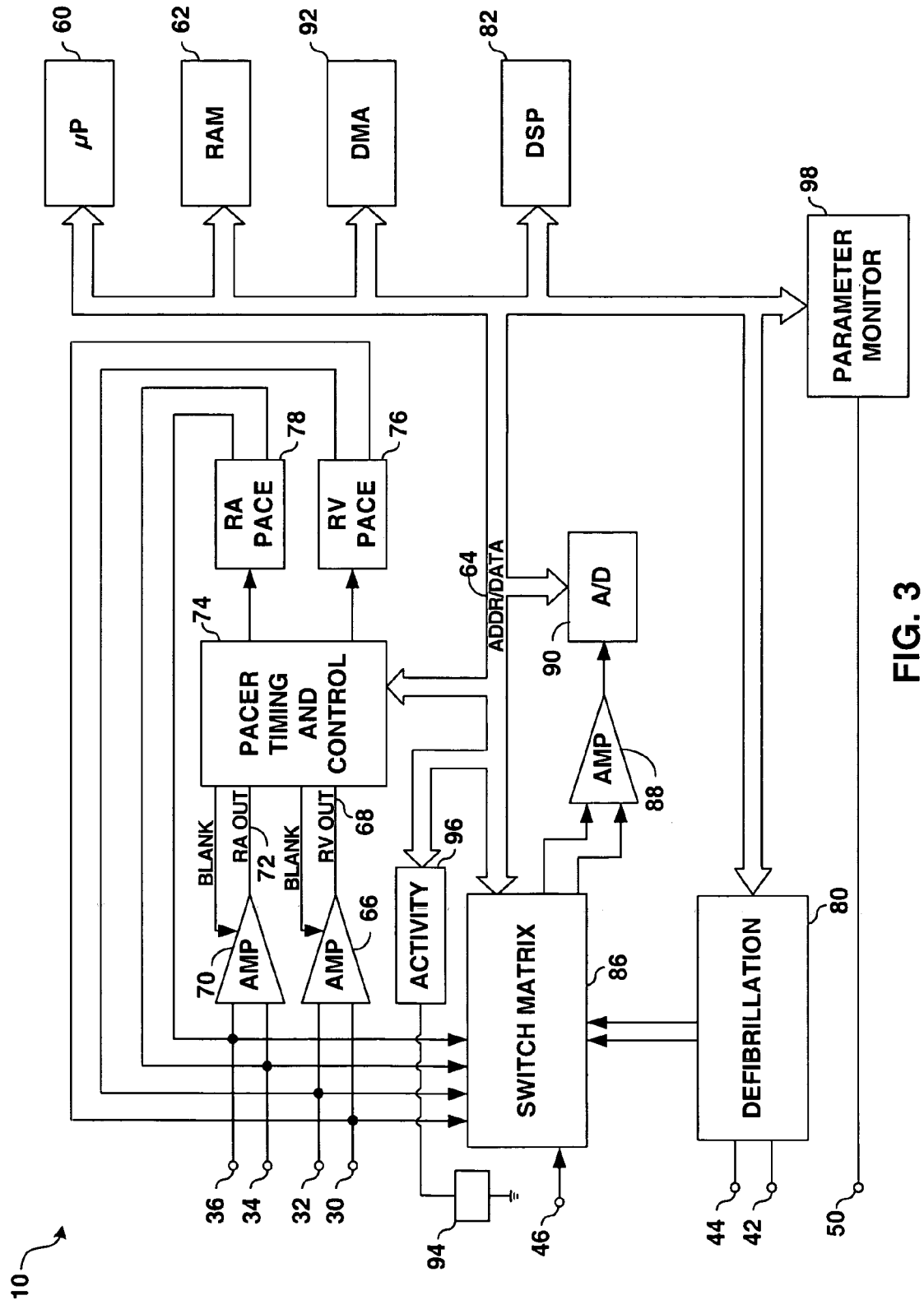
FIG. 3 is a functional block diagram illustrating the implantable medical device of FIG. 1 in greater detail.

FIG. 3 is a functional block diagram of IMD 10. In the illustrated embodiment, IMD 10 takes the form of a multichamber pacemaker with cardioversion and/or defibrillation capability having a microprocessor-based architecture. However, this diagram should be taken as exemplary of the type of device in which various embodiments of the present invention may be embodied, and not as limiting. For example, some embodiments of the invention provide no defibrillation or cardioversion therapy, but instead are pacemakers that provide anti-tachycardia pacing (ATP) to treat detected arrhythmias.

IMD 10 includes a microprocessor 60. Microprocessor 60 executes program instructions stored in memory, such as a ROM (not shown), EEPROM (not shown), and/or RAM 62, which control microprocessor 60 to perform the functions ascribed to microprocessor 60 herein. Microprocessor 60 is coupled to, e.g., communicates with and/or controls, various other components of IMD 10 via an address/data bus 64.

Electrodes 30 and 32 are coupled to amplifier 66, which takes the form of an automatic gain controlled amplifier providing an adjustable sensing threshold as a function of the measured R-wave amplitude. A signal is generated on RV out line 68 whenever the signal sensed between electrodes 30 and 32 exceeds the present sensing threshold. Electrodes 34 and 36 are coupled to amplifier 70, which also takes the form of an automatic gain controlled amplifier providing an adjustable sensing threshold as a function of measured P-wave amplitude. A signal is generated on RA out line 72 whenever the signal sensed between electrodes 34 and 36 exceeds the present sensing threshold.

IMD 10 paces heart 16. Pacer timing/control circuitry 74 includes programmable digital counters which control the basic time intervals associated with modes of pacing. Pacer timing/control circuitry 74 also controls escape intervals associated with pacing. In the exemplary two-chamber pacing environment, pacer timing/control circuitry 74 controls the atrial and ventricular escape intervals that are used to time pacing pulses delivered to right atrium 18 and right ventricle 20.

Intervals defined by pacer timing/control circuitry 74 also include the refractory periods during which sensed R-waves and P-waves are ineffective to restart timing of the escape intervals, and the pulse widths of the pacing pulses. The durations of these intervals are determined by microprocessor 60 in response to data stored in RAM 62, and are communicated to circuitry 74 via address/data bus 64. Pacer timing/control circuitry 74 also determines the amplitude of the cardiac pacing pulses under control of microprocessor 60.

During pacing, escape interval counters within pacer timing/control circuitry 74 are reset upon sensing of R-waves and P-waves as indicated by signals on lines 68 and 72, and, in accordance with the selected mode of pacing, circuitry 74 controls generation and delivery of pacing pulses upon timeout of the escape intervals. Circuitry 74 also resets escape interval counters upon generation of pacing pulses. Circuitry 74 uses the value of the count present in escape interval counters when reset by sensed R-waves and P-waves, or delivered pacing pulses, to measure ventricular cycle lengths (VCLs) and, in some embodiments, atrial cycle lengths (ACLs). Circuitry 74 provides the measured VCL and ACL values to microprocessor 60 for detection of arrhythmias, which will be described in greater detail below, via address/data bus 64.

Microprocessor 60 operates as an interrupt driven device, and is responsive to interrupts from pacer timing/control circuitry 74 corresponding to the occurrence of sensed P-waves and R-waves and corresponding to the generation of cardiac pacing pulses. Those interrupts are provided via data/address bus 64. Any necessary mathematical calculations to be performed by microprocessor 60 and any updating of the values or intervals controlled by pacer timing/control circuitry 74 take place following such interrupts.

In accordance with the selected mode of pacing, pacer timing/control circuitry 74 triggers generation of pacing pulses by one or more of pacer output circuits 76 and 78, which are coupled to electrodes 30 and 32, and 34 and 36, respectively. Output circuits 76 and 78 are pulse generation circuits, which include capacitors and switches for the storage and delivery of energy as a pulse.

In some embodiments, IMD 10 detects ventricular arrhythmias using tachycardia and fibrillation detection techniques and algorithms described above with reference to FIG. 1. For example, RAM 62 can store NID thresholds for various ventricular arrhythmias, and microprocessor 60 can detect ventricular arrhythmias by receiving VCLs from pacer timing/control circuitry 74, categorizing the VCLs based on VCL ranges for the various types of arrhythmias, and counting VCLs within each category. A clinician can program values for the VCL ranges and NIDs via a programming device and device telemetry, as is well known in the art. NIDs stored by RAM 62 can include a VF NID, VT NID, FVT NID, and a combined count NID in which intervals classified as VF or VT are considered together.

In response to detection of an arrhythmia, IMD 10 is capable of delivering one or more anti-tachycardia pacing (ATP) therapies to heart 16, and/or defibrillation or cardioversion shocks to heart 16 via one or more of electrodes 30-36 and 42-46. Electrodes 42 and 44 are coupled to defibrillation circuit 80, which delivers defibrillation and/or cardioversion pulses under the control of microprocessor 60. Defibrillation circuit 80 includes energy storage circuits such as capacitors, switches for coupling the storage circuits to coil electrodes 42 and 44, and logic for controlling the coupling of the storage circuits to the electrodes to create pulses with desired polarities and shapes. Microprocessor 60 may employ an escape interval counter to control timing of such defibrillation pulses, as well as associated refractory periods.

A clinician can program therapies or sequences of therapies for each of the types of ventricular arrhythmias via a programming device and device telemetry, and information describing the programmed therapies and/or sequences of therapies can be stored in RAM 62. The programmed therapies can include sequences of one or more defibrillation pulses, one or more cardioversion pulses, one or more ATP attempts, or combinations thereof.

As described above, when microprocessor 60 determines that a NID for a ventricular arrhythmia is met based on measured VCLs, microprocessor 60 further determines whether the ventricular rhythm is a suspected non-lethal arrhythmia, e.g., an SVT, monomorphic VT, or a rhythm causes by cardiac or non-cardiac oversensing. In some embodiments, for example, microprocessor 60 determines the median or mean VCL and ACL, e.g., over the last 4-20 beats, and compares the values to determine if the rhythm is suspected non-lethal. In such embodiments, microprocessor 60 determines that the rhythm is a suspected non-lethal arrhythmia when median or mean ACL is substantially equal to or greater than the median or mean VCL. When the ACL is substantially equal to or greater than the VCL, it is more likely that the fast ventricular rhythm is caused by an SVT. RAM 62 can store a suspect threshold value, and microprocessor 60 can compare the difference or ratio between the VCL and ACL to the threshold value to determine whether the rhythm is suspect.

In some embodiments, RAM 62 stores a minimum VCL threshold for suspected non-lethal arrhythmias, e.g., 270 milliseconds. In such embodiments, microprocessor 60 compares the mean or median VCL to the minimum VCL, and only indicates that the rhythm is suspect if the VCL value exceeds the threshold value. In other words, certain fast rhythms should be treated without delay and with an originally scheduled therapy despite other analysis indicating that the rhythm is suspected non-lethal.

In other embodiments, microprocessor 60 additionally or alternatively analyzes the regularity of measured VCLs and/or morphological features the ventricular rhythm to determine whether the arrhythmia is suspected non-lethal. Microprocessor 60 can, for example, calculate the variability of measured VCLs over the previous 10 intervals, and the morphological analysis can include, for example, an analysis of the width of ventricular depolarizations and/or a wavelet analysis.

In some embodiments, microprocessor 60 additionally or alternatively analyzes the level of association between the occurrence of atrial and ventricular depolarizations, e.g., the level of A:V association, and/or the rate of onset within measured ACLs, VCLs, and/or A-V intervals to determine whether the arrhythmia is suspected non-lethal. A relatively high level of A:V association, or a relatively slow rate of onset of measures ACLs, VCLs, and/or A-V intervals can indicate the presence of an SVT such as sinus tachycardia.

In exemplary embodiments, a ventricular electrogram (EGM) signal received via a combination of any of electrodes 30, 32 and 46 is digitally processed by a digital signal processor (DSP) 82 for morphological analysis of the signal. In such embodiments, switch matrix 84 is used to select which of electrodes 30, 32 and 46 are coupled to wide band (0.5-200 Hz) amplifier 86 for use in digital signal analysis. Selection of electrodes is controlled by microprocessor 60 via data/address bus 66, and the selections may be varied as desired. The EGM signal is converted to a digital signal by analog to digital converter circuit 88, and provided to DSP 82 via address/data bus 66. In some embodiments, the digital signal is stored in RAM 62, and retrieved there from by DSP 82 for analysis. In other embodiments, IMD 10 does not include a dedicated DSP 82, and microprocessor 60 performs the digital signal analysis described herein.

Substantial irregularity of measured VCLs and/or ventricular electrogram morphology can be caused by an SVT. However, substantial regularity of measured VCLs and/or ventricular electrogram morphology can indicate a monomorphic VT. In both cases, the regularity of measured VCLs and/or the electrogram morphology is used to detect or confirm that a ventricular arrhythmia is a suspected non-lethal arrhythmia.

IMD 10 is shown in FIG. 3 as including an activity sensor 94. In some embodiments, microprocessor 60 additionally or alternatively determines whether a rhythm is a suspected non-lethal arrhythmia based on the activity level of patient 12.

For example, and high activity level can indicate that the fast ventricular rhythm is a sinus tachycardia caused by patient 12 exercising, and therefore a suspected non-lethal arrhythmia.

Activity sensor 94 typically (although not necessarily) provides a sensor output that varies as a function of a measured parameter relating to metabolic requirements of patient 12. In exemplary embodiments, activity sensor 94 is a piezoceramic accelerometer bonded to a hybrid circuit located inside housing 48 (FIG. 2). In other embodiments, activity sensor 94 additionally or alternatively comprises electrodes to detect respiration rate of patient 12 via cyclical variations in the thoracic impedance of patient 12. The output signal provided by activity sensor 94 is coupled to an activity detection circuit 96, which determines the activity level, e.g., counts, of patient 12 based on the output. The activity level or counts are provided to microprocessor 60, which determines whether a ventricular rhythm that meets an initial NID for an arrhythmia is in fact a suspected non-lethal based on the activity level.

In the illustrated example, IMD 10 also includes a parameter monitor circuit 98. Parameter monitor circuit 98 processes the signal received from sensor 50, and provides a result of the processing to microprocessor 60 for use in determining whether a fast ventricular rhythm is a suspected non-lethal arrhythmia. In exemplary embodiments where sensor 50 is an intracardiac pressure sensor, monitor circuit 94 processes the pressure signal to provide information indicating intracardiac pressure values to microprocessor 60. Microprocessor 60 can, for example, analyze the pressure values to determine whether the intracardiac pressure is stable. A stable pressure can indicate that the rhythm is suspected non-lethal, while an unstable pressure can indicate that treatment of the rhythm should not be delayed or altered. Intracardiac pressures often remain stable during, SVTs, slower monomorphic VTs, and when an arrhythmia is incorrectly identified due to cardiac or non-cardiac oversensing.

In response to determining that a rhythm that meets the NID for an arrhythmia is a suspected non-lethal arrhythmia, microprocessor 60 can take a variety of actions to delay delivery of or change a therapy scheduled for delivery in response to detection of that arrhythmia. For example, microprocessor 60 can increase the NID and monitor subsequent VCLs to determine if the rhythm meets the increased NID. As another example, microprocessor can change the ventricular therapy scheduled for the initially detected arrhythmia.

In some embodiments, the microprocessor 60 further determines whether a suspected non-lethal arrhythmia is a slow suspected non-lethal arrhythmia. In such embodiments, microprocessor 60 by determining whether the median or mean VCL is greater than a slow suspected non-lethal threshold value, e.g., 370 milliseconds. RAM 62 stores the slow suspected non-lethal threshold value.

In such embodiments, microprocessor 60 can treat slow suspected non-lethal arrhythmias differently than other suspected non-lethal arrhythmias because they are presumed to pose even less of a risk to the patient than other suspected non-lethal arrhythmias. In particular, microprocessor 60 can increase the NID threshold by a greater amount for slow suspected rhythms than other suspected rhythms and/or provide a different therapy change for slow suspected rhythms than other suspected rhythms. For example, where the microprocessor 60 would reduce the number of defibrillation or cardioversion shocks and add ATP attempts for suspected non-lethal arrhythmias, microprocessor 60 can eliminate the shocks and instead deliver ATP alone for if the suspected non-lethal arrhythmia is a slow suspected non-lethal arrhythmias. In some embodiments, the microprocessor 60 can simply withhold delivery of any therapies based on the determination that the rhythm is a slow suspected non-lethal arrhythmia, i.e., can extend the NID and detect based on the extended NID without delivery of therapy upon detection, or can simply reset the NID upon a determination that the rhythm is a slow suspected non-lethal arrhythmia.

Although IMD 10 is described herein as having separate processors, microprocessor 60 may perform both the functions ascribed to it herein and digital signal analysis functions ascribed to DSP 82 herein. Moreover, although described herein in the context of microprocessor-based pacemaker embodiment IMD 10, the invention may be embodied in various implantable medical devices that include one or more processors, which may be microprocessors, DSPs, FPGAs, or other digital logic circuits.

Figure 4:
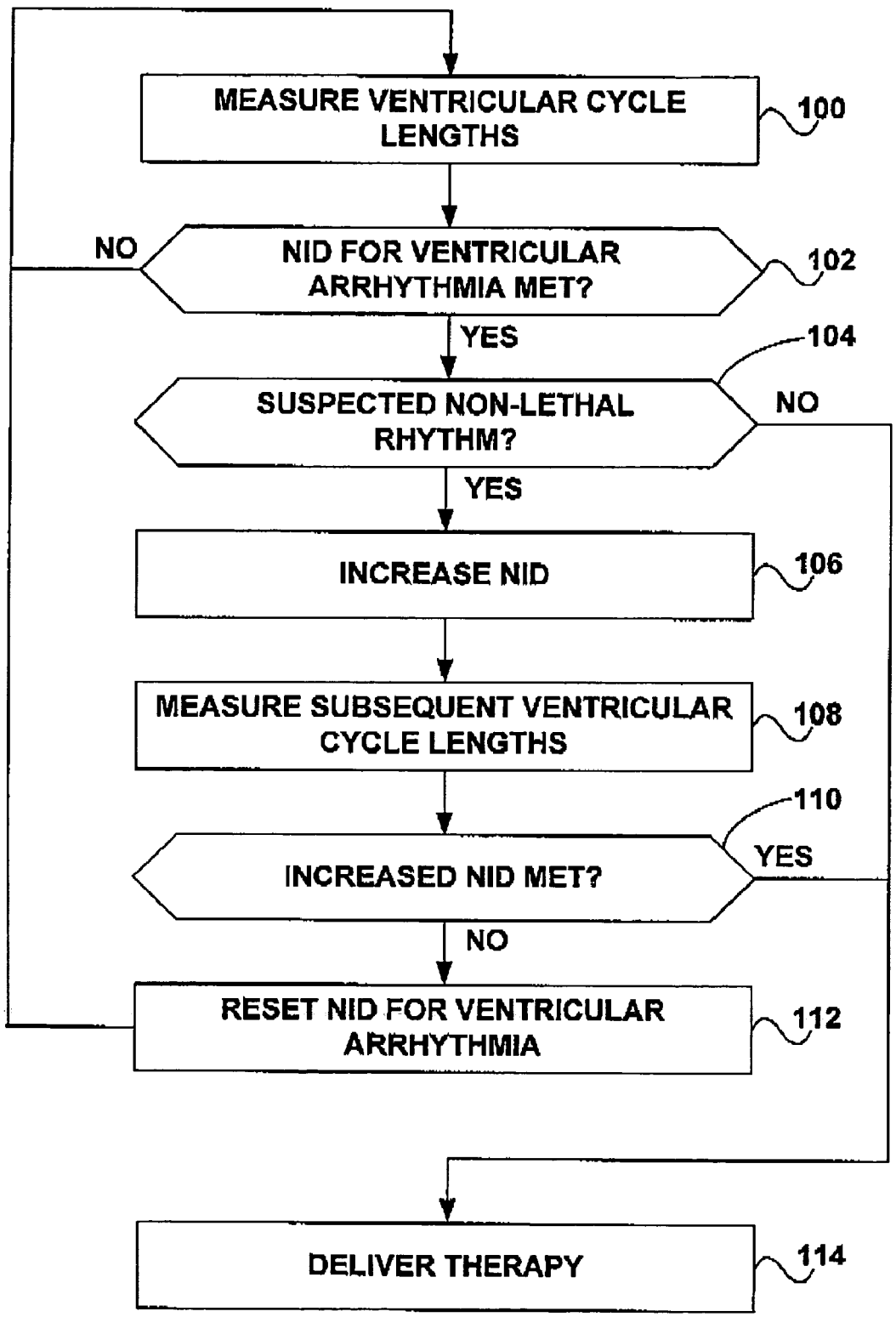
FIG. 4 is a flow diagram illustrating an example technique employed by the implantable medical device of FIG. 1 to reduce inappropriate delivery of therapy for suspected non-lethal arrhythmias by increasing a number of intervals to detect threshold.

FIG. 4 is a flow diagram illustrating an example technique employed by IMD 10 to reduce inappropriate delivery of therapy for suspected non-lethal arrhythmias by increasing a NID threshold. Microprocessor 60 measures VCLs within a ventricular rhythm (100), and determines whether a NID for an arrhythmia is met (102). When the NID for a ventricular arrhythmia is met, microprocessor 60 further determines whether the rhythm is a suspected non-lethal arrhythmia using any of the techniques described above (104).

If microprocessor 60 determines that the rhythm is not suspect, microprocessor 60 controls delivery of therapy (114) by, for example, controlling delivery of a defibrillation shock via defibrillation circuit 80. However, if microprocessor 60 determines that the rhythm is a suspected non-lethal arrhythmia, microprocessor 60 increases the NID (106), and measures subsequent VCLs (108) to determine whether the increased NID is met (110). In some embodiments, microprocessor 60 compares a median or mean VCL to a median or mean ACL, and determines whether the rhythm is suspect based on the comparison. In some embodiments, a clinician programs the initial NID and the amount of increase for the NID. In other embodiments, microprocessor 60 adaptively determines the amount of increase for the NID based on the VCL/ACL comparison, e.g., the difference between the VCL and ACL, the median or mean VCL itself, and/or a measured value of a physiological parameter such as an intracardiac pressure. RAM 62 can store information for the determination of NID increase, such as a function or look-up table.

Increasing the NID can include increasing an amount of time, a number of intervals, or both. Because combined count NIDs include a number of "look-back" beats, i.e., a number of previous intervals to review to determine whether a an arrhythmia detected via the combined count is a fibrillation or tachycardia, Increasing a combined count NID can also include increasing a number of look-back beats. If the increased NID is met (110), microprocessor 60 can control delivery of a ventricular therapy scheduled for the detected arrhythmia (114). However, if the increased NID is not met, microprocessor 60 can reset the NID for the initially detected arrhythmia to its original value (112).

In some embodiments, when the increased NID is met microprocessor 60 again determines whether the rhythm is a suspected non-lethal arrhythmia, and can further increase the NID. The second and subsequent increases to the NID can be of a different amount than each other and first NID increase, e.g., the amount of the increases to the NID can iteratively increase or decrease.

Figure 5:
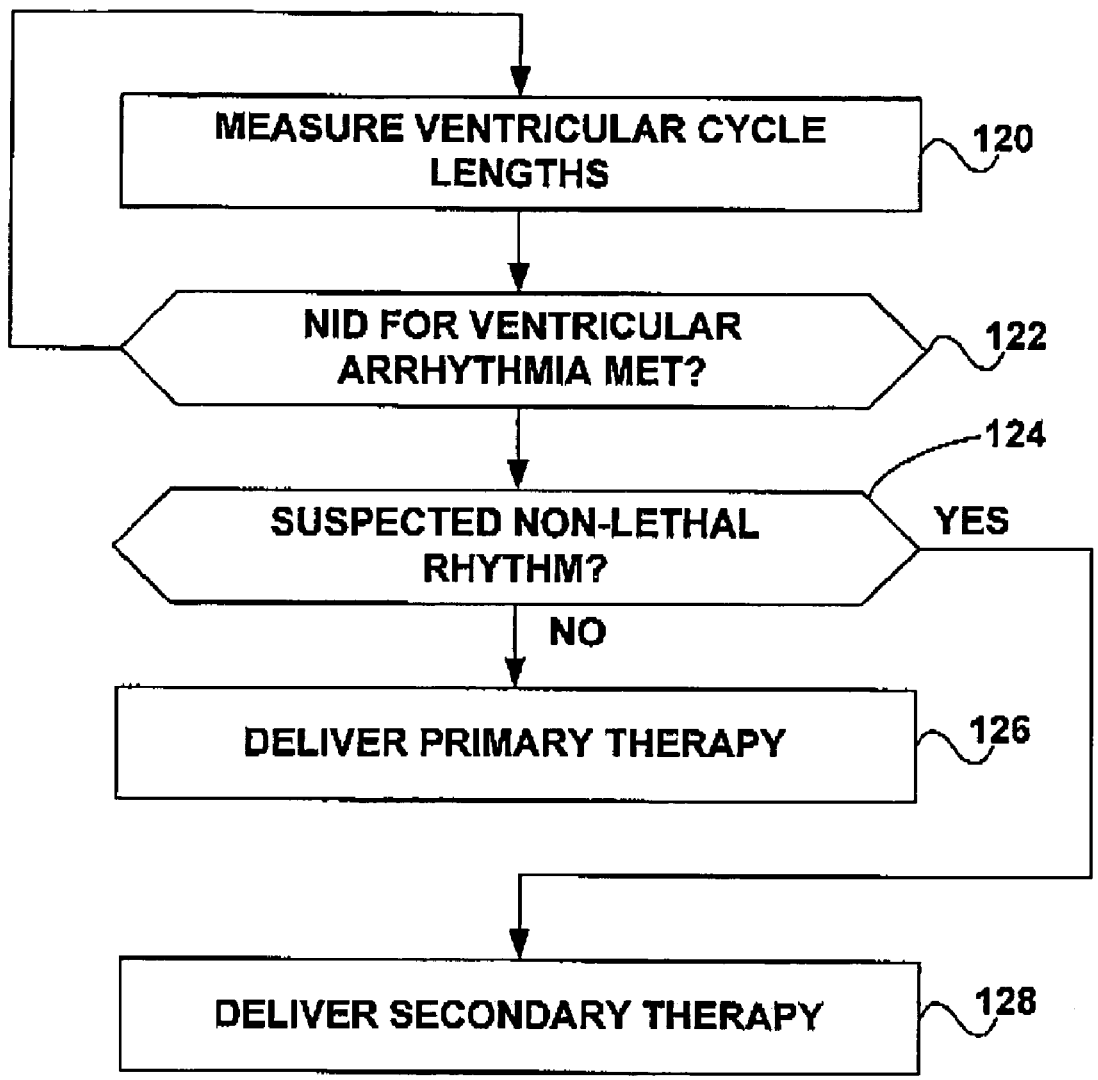
FIG. 5 is a flow diagram illustrating an example technique employed by the implantable medical device of FIG. 1 to reduce inappropriate delivery of therapy for suspected non-lethal arrhythmias by changing a ventricular therapy scheduled for the arrhythmia.

FIG. 5 is a flow diagram illustrating an example technique employed by IMD 10 to reduce inappropriate delivery of therapy for suspected non-lethal arrhythmias by changing a ventricular therapy scheduled for the arrhythmia. Microprocessor 60 measures VCLs within a ventricular rhythm (120), and determines whether a NID for an arrhythmia is met (122). When the NID for a ventricular arrhythmia is met, microprocessor 60 further determines whether the rhythm is a suspected non-lethal arrhythmia using any of the techniques described above (124).

If microprocessor 60 determines that the rhythm is not suspect, microprocessor 60 controls delivery of the primary therapy scheduled for that arrhythmia (126). However, if microprocessor 60 determines that the rhythm is a suspected non-lethal arrhythmia, microprocessor 60 changes the ventricular therapy scheduled for that arrhythmia to a secondary ventricular therapy, and controls delivery of the secondary ventricular therapy (128). A clinician can program the primary and secondary therapies.

For example, where a sequence of one or more defibrillation of cardioversion shocks was scheduled as the primary therapy to be delivered in response to detection of a VF or VT, the secondary therapy can include a reduced number of shocks in the sequence or can replace some or all of the shocks with one or more anti-tachycardia pacing (ATP) attempts for ventricles 20 and 22. Where delivery of ATP attempts to ventricles 20 and 22 was scheduled as the primary therapy, the secondary therapy can include a reduced or increased number of ATP attempts. In some embodiments, the secondary therapy includes a therapy sequence that is similar to the primary therapy but with different parameters, e.g., different shock energy levels or pathways, or different ATP ramp rates than the primary therapy.

In some embodiments, microprocessor 60 additionally controls delivery of therapy, such as ATP, to atria 18 and 24 upon a determination that a ventricular rhythm is a suspected non-lethal arrhythmia. Delivery of atrial therapy may terminate an underlying SVT where an SVT is suspected as the cause of the detected fast ventricular rhythm.

Figure 6:
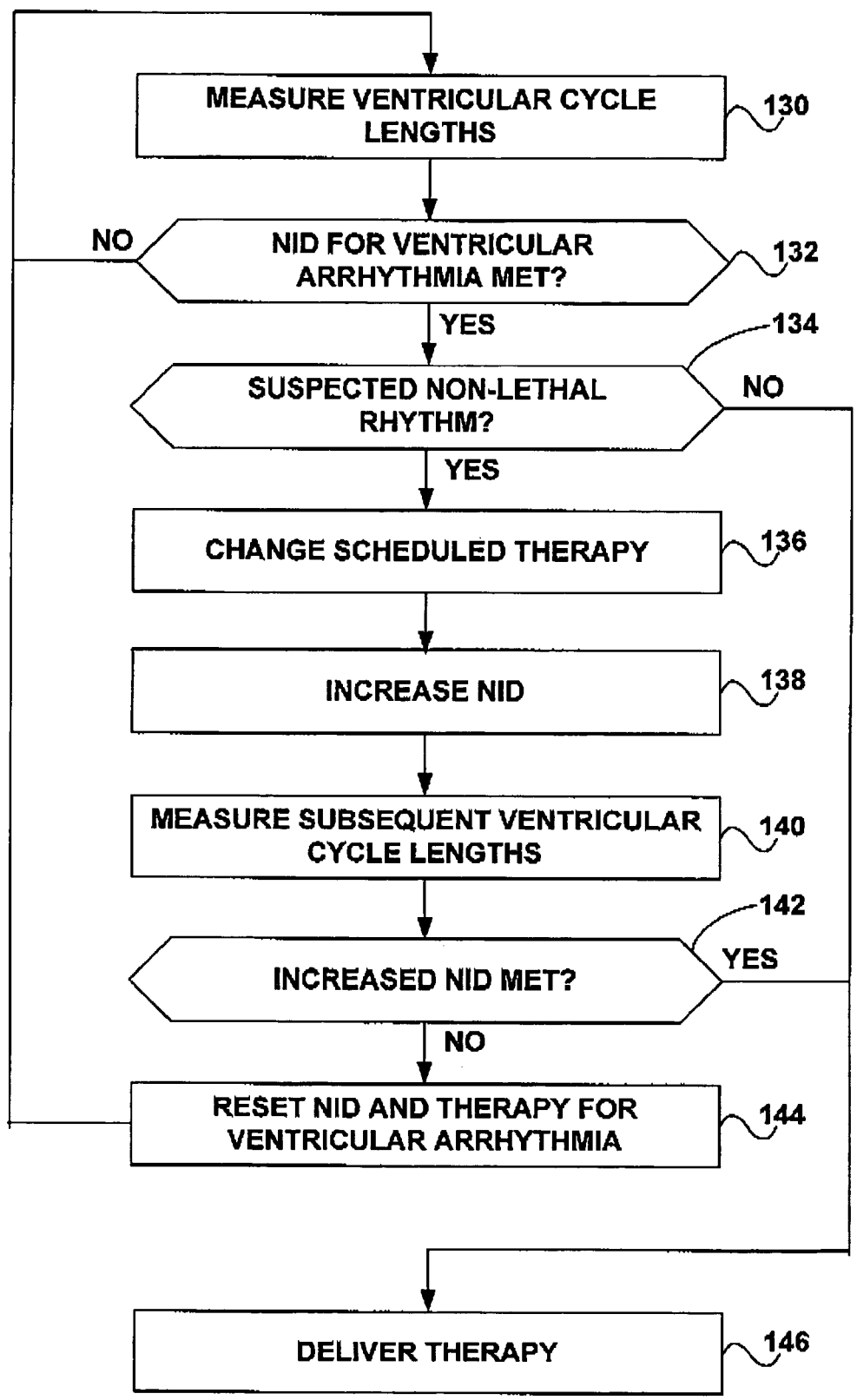
FIG. 6 is a flow diagram illustrating an example technique employed by the implantable medical device of FIG. 1 to reduce inappropriate delivery of therapy for suspected non-lethal arrhythmias by combining the techniques of FIGS. 4 and 5.

FIG. 6 is a flow diagram illustrating an example technique employed by IMD 10 to reduce inappropriate delivery of therapy for suspected non-lethal arrhythmias by combining the techniques of FIGS. 4 and 5. Microprocessor 60 measures VCLs within a ventricular rhythm (130), and determines whether a NID for an arrhythmia is met (132). When the NID for a ventricular arrhythmia is met, microprocessor 60 further determines whether the rhythm is a suspected non-lethal arrhythmia using any of the techniques described above (134).

If microprocessor 60 determines that the rhythm is not suspect, microprocessor 60 controls delivery of therapy scheduled for the detected arrhythmia (146). However, if microprocessor 60 determines that the rhythm is a suspected non-lethal arrhythmia, microprocessor 60 changes the scheduled therapy as described above (136), and increases the NID (138). Microprocessor 60 then measures subsequent VCLs (140) to determine whether the increased NID is met (142). If the increased NID is met, microprocessor controls delivery of the scheduled therapy of the arrhythmia as changed (146). However, if the increased NID is not met, microprocessor 60 resets the NID and the scheduled therapy to their initial values (144).

In some embodiments, microprocessor 60 additionally controls delivery of therapy, such as ATP, to atria 18 and 24 upon a determination that a ventricular rhythm is a suspected non-lethal arrhythmia. Where the fast ventricular rhythm is caused by an SVT, delivery of atrial therapy may terminate the underlying SVT during the period in which the NID is extended, preventing inappropriate delivery of therapy at the end of the extended NID. Further, increasing the NID with or without delivery of atrial therapy allows time for the initially detected arrhythmia, whether it is an SVT or monomorphic VT, to spontaneously terminate without delivery of ventricular shocks and the attendant patient discomfort. Changing the originally scheduled therapy, e.g., from shocks to ATP, can also reduce patient discomfort by avoiding delivery of shocks, both in embodiments where the NID is increased (FIG. 6) and in embodiments where the changed therapy is delivered immediately upon a determination that the rhythm is a suspected non-lethal arrhythmia (FIG. 5).

Figure 7:
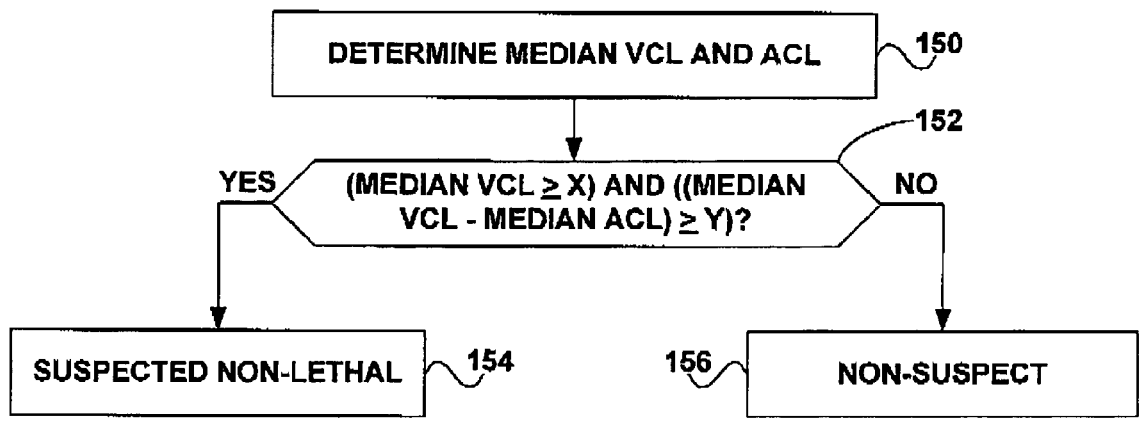
FIG. 7 is a flow diagram illustrating an example technique employed by the implantable medical device of FIG. 1 to determine whether a ventricular rhythm is a suspected non-lethal arrhythmia.

FIG. 7 is a flow diagram illustrating an example technique employed by IMD 10 to determine whether a ventricular rhythm is a suspected non-lethal arrhythmia. In particular, FIG. 7 illustrates an example technique employed by IMD 10 to determine whether a ventricular rhythm is a suspected SVT. IMD 10 determines the median VCL and ACL for a number of previous intervals, e.g., the ten intervals, that preceded the interval in which a NID for an arrhythmia is met (150). If the median VCL is greater than or equal to a minimum VCL threshold ("X") for suspected non-lethal arrhythmias, and the difference between the median VCL and median ACL is greater than or equal to a suspect threshold ("Y") (152), microprocessor 60 determines that the rhythm in question is a suspected non-lethal arrhythmia (154). If either of the thresholds is not met, microprocessor 60 determines that the rhythm is non-suspect, and proceeds to deliver a ventricular therapy scheduled for the detected arrhythmia (156).

RAM 62 stores the threshold values. In exemplary embodiments, the minimum VCL threshold ("X") is approximately 270 milliseconds, while the suspect threshold ("Y") is equal to −30 milliseconds. In some embodiments, the suspect threshold is set at a small negative value so that ventricular rhythms with a median VCL that is approximately equal to or greater than the median ACL are identified as suspect. Although atrial fibrillation and atrial flutter generally results in a median VCL that is significantly greater than the median ACL, other SVTs such as sinus tachycardia and atrial tachycardia can result in a median VCL that is slightly less than the median ACL. In some embodiments, microprocessor 60 uses a mean VCL and mean ACL instead of the median values.

Instead of or in addition to determining that a ventricular arrhythmia is a suspected SVT, in some embodiments IMD 10 determines whether the rhythm is a suspected non-lethal arrhythmia by determining whether the rhythm is a monomorphic VT. In such embodiments, microprocessor 60 analyzes the regularity of the VCL lengths and/or the regularity of the morphological features of the rhythm, as described above, instead of or in addition to comparing median VCLs to median ACLs. In such embodiments, microprocessor 60 can also apply a minimum VCL threshold stored by RAM 62 so that fast and potentially dangerous arrhythmias are treated upon satisfaction of the initial NID with the scheduled therapy. A monomorphic VT minimum VCL threshold can be the same as an SVT minimum VCL threshold, e.g., 270 milliseconds, or can be slightly longer, e.g., 300 milliseconds, because fast monomorphic VTs can pose greater risk to patient 12 then a ventricular rhythm of with the same median VCL caused by an SVT.

In some embodiments, IMD 10 additionally or alternatively determines whether the NID threshold for a ventricular arrhythmia has been met in error due to cardiac or non-cardiac oversensing. Cardiac oversensing can for example be caused by T-wave oversensing, while non-cardiac oversensing is caused by noise within a detected cardiac signal, such as noise caused by lead failure, a loose set screw, or the like. When microprocessor 60 identifies cardiac or non-cardiac oversensing, microprocessor 60 classifies the ventricular rhythm as a suspected non-lethal cardiac rhythm.

Cardiac and non-cardiac oversensing can result in very short measured VCLs, and microprocessor 60 can identify cardiac and non-cardiac oversensing by determining that a median or mean VCL is less than or equal to an oversensing threshold value. RAM 62 stores the oversensing threshold value, which in exemplary embodiments is approximately 180 milliseconds. In some embodiments, microprocessor 60 identifies cardiac or non-cardiac oversensing by applying techniques described in commonly-assigned U.S. patent application Ser. No. 10/135,080 by Gunderson et al., filed Apr. 29, 2002.

In response to identifying cardiac or non-cardiac oversensing, microprocessor 60 can increase the NID threshold and/or modify a scheduled therapy as described above. The amount the microprocessor 60 increases the NID threshold and/or the change to the therapy applied by microprocessor 60 upon identification of cardiac or non-cardiac sensing can be the same as or different than the increases and/or changes applied when a potential SVT or monomorphic VT is detected as a suspected non-lethal arrhythmia. In exemplary embodiments, the microprocessor 60 applies a greater amount of NID threshold increase when a oversensing is suspected than when SVT or monomorphic VT is suspected. For example, where oversensing is suspected, microprocessor can increase the NID threshold by to three to five times its original value.

Figure 8:
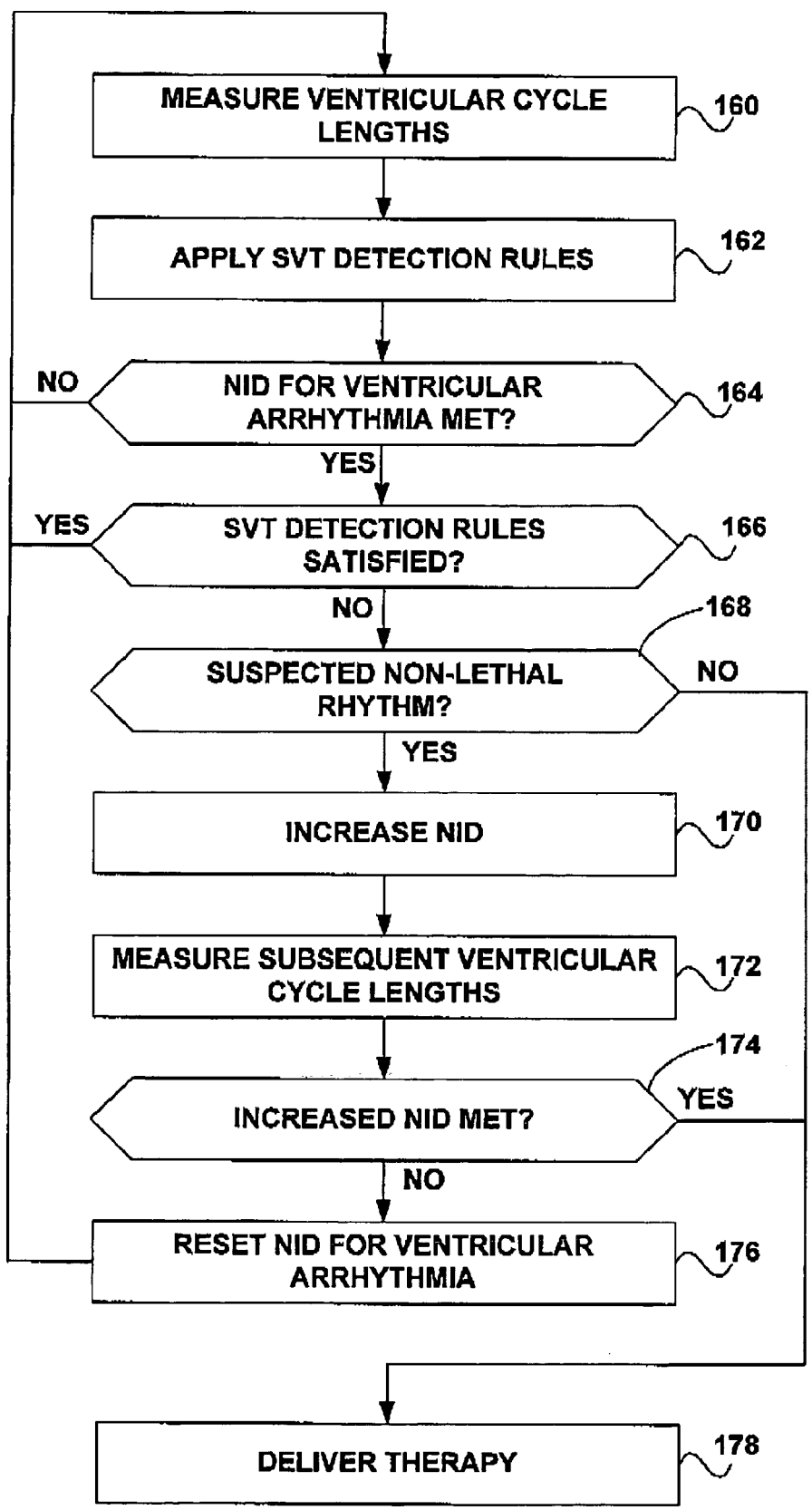
FIG. 8 is a flow diagram illustrating an example technique employed by the implantable medical device of FIG. 1 to reduce inappropriate delivery of therapy for suspected non-lethal arrhythmias that includes application of separate, specific SVT detection rules.

FIG. 8 is a flow diagram illustrating an example technique employed by IMD 10 to reduce inappropriate delivery of therapy for suspected non-lethal arrhythmias that includes application of separate, specific SVT detection rules. In some embodiments IMD 10, and more particularly microprocessor 60, applies specific SVT detection rules to determine if an SVT is the cause of the fast ventricular rhythm. For example, if a NID is met during a particular ventricular interval and the further analysis indicates the presence of a confirmed SVT, IMD 10 can avoid detection of VF or VT during that interval and wait to analyze the next ventricular interval and determine the unchanged NID continues to be met.

However, as described above, such specific SVT rules often fail to correctly identify SVTs despite such additional analysis, and consequently too often allow inappropriate delivery of therapy to occur. Such SVT detection rules fail to detect SVTs because they are designed to favor prompt delivery or therapy and result in no false positive SVT detections. SVT detection rules can include analysis of A-V and V-A interval patterns, comparison of ACLs and VCLs, detection of A:V dissociation, analysis of VCL regularity. An exemplary set of specific SVT detection rules is provided by pacemakers manufactured by Medtronic, Inc. and identified by the trade name PR-Logic™.

FIG. 8 illustrates an example technique wherein microprocessor 60 determines whether a ventricular rhythm is a suspected non-lethal arrhythmia subsequent to application of specific SVT detection rules, allowing IMD 10 to avoid delivery of therapy in cases where the SVT detection rules would fail to positively identify an SVT. Microprocessor 60 measures VCLs within a ventricular rhythm (160), and determines whether a NID for an arrhythmia is met (162). When the NID for a ventricular arrhythmia is met, microprocessor 60 applies the SVT detection rules (164).

If the SVT detection rules are satisfied (166), microprocessor 60 measures the next VCL and determines whether the unchanged NID for the ventricular arrhythmia is still met (162). However, if the SVT detection rules are not satisfied, microprocessor 60 further determines whether the rhythm is a suspected non-lethal arrhythmia using any of the techniques described above (168). In some embodiments, microprocessor 60 determines whether the rhythm is suspect prior to application of the SVT detection rules rather than after failure of the SVT rules to detect an SVT. By applying the SVT rules and the suspect determination analysis in this order, microprocessor 60 can avoid unnecessary application of such computational intensive rules and, to the extent that the rhythm is determined to be suspect, allow more time for the rhythm to spontaneously terminate.

If microprocessor 60 determines that the rhythm is not suspect, microprocessor 60 controls delivery of a therapy scheduled for the detected arrhythmia (178). However, if microprocessor 60 determines that the rhythm is a suspected non-lethal arrhythmia, microprocessor 60 increases the NID threshold for the arrhythmia (170), and measures subsequent VCLs (172) to determine whether the increased NID is met (174). If the increased NID is met, microprocessor 60 can control delivery of a ventricular therapy scheduled for the detected arrhythmia (178). However, if the increased NID is not met, microprocessor 60 can reset the NID for the initially detected arrhythmia to its original value (176).

Figure 9:
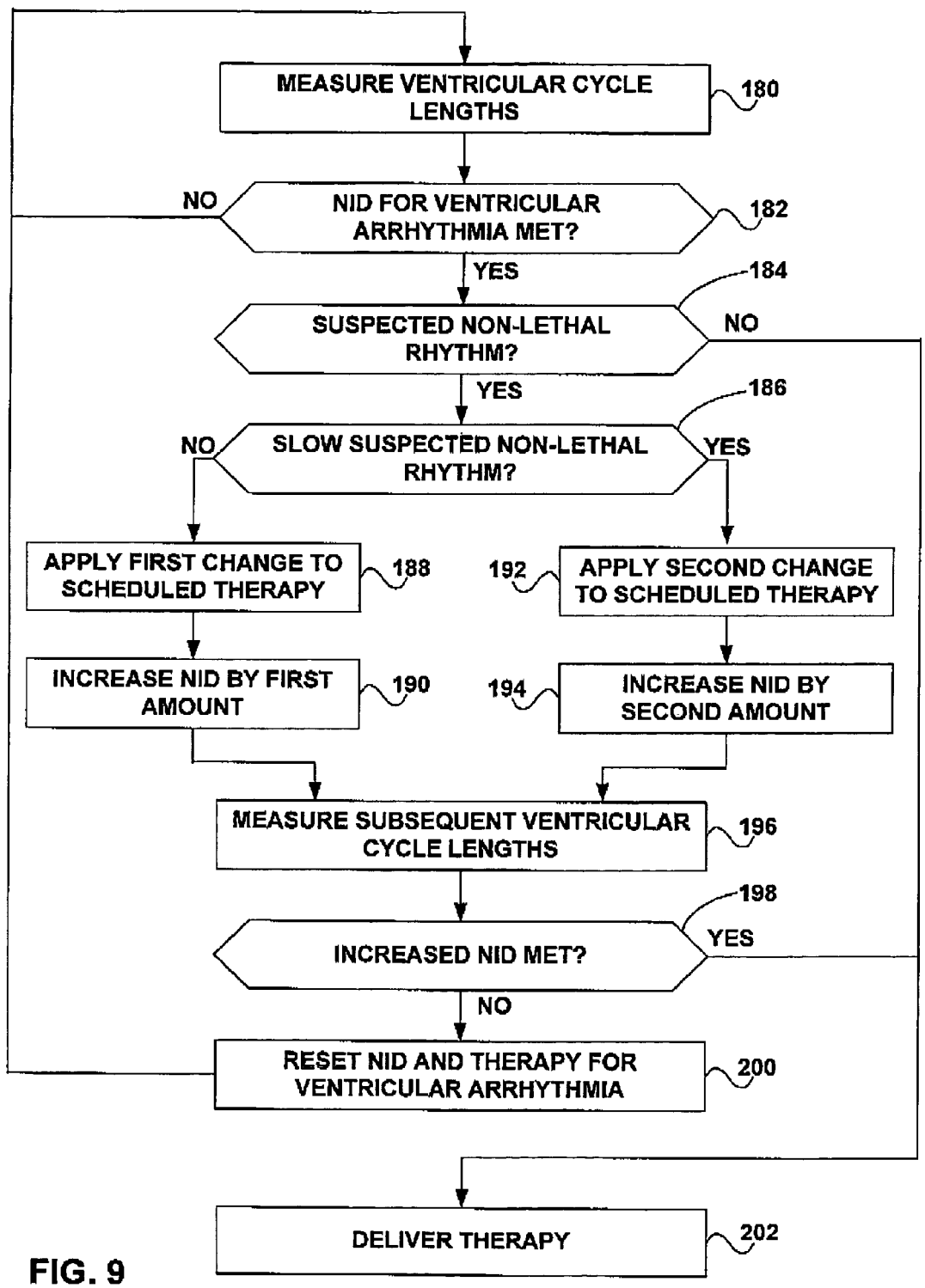
FIG. 9 is a flow diagram illustrating an example technique employed by the implantable medical device of FIG. 1 to reduce inappropriate delivery of therapy for suspected non-lethal arrhythmias that includes further classification of suspected non-lethal arrhythmias as slow suspected non-lethal arrhythmias.

FIG. 9 is a flow diagram illustrating an example technique employed by IMD 10 to reduce inappropriate delivery of therapy for suspected non-lethal arrhythmias that includes further classification of suspected non-lethal arrhythmias as slow suspected non-lethal arrhythmias. In such embodiments, IMD 10 treats slow suspected non-lethal arrhythmias differently than other suspected non-lethal arrhythmias because they are presumed to pose less of a risk to the patient. As will be described in greater detail below, IMD 10 determines whether a suspected non-lethal arrhythmia is a slow suspected non-lethal arrhythmia based on a comparison of a median or mean VCL to a slow suspected non-lethal arrhythmia threshold value. When IMD 10 combines this comparison with a comparison of the median or mean VCL to the minimum suspected non-lethal arrhythmia threshold and oversensing threshold described above, IMD 10 creates four VCL zones for detected arrhythmias in which the arrhythmias can be treated differently.

Microprocessor 60 measures VCLs within a ventricular rhythm (180), and determines whether a NID for an arrhythmia is met (182). When the NID for a ventricular arrhythmia is met, microprocessor 60 further determines whether the rhythm is a suspected non-lethal arrhythmia using any of the techniques described above (184).

If microprocessor 60 determines that the rhythm is not suspect, microprocessor 60 controls delivery of a scheduled therapy for the detected ventricular arrhythmia (202). However, if microprocessor 60 determines that the rhythm is suspect, microprocessor 60 further determines whether the rhythm is a slow suspected non-lethal tachycardia (186). If microprocessor 60 determines that the rhythm is not a slow suspected non-lethal arrhythmia, microprocessor 60 applies a first change to a scheduled therapy (188) and increases the NID threshold by a first amount (190). If microprocessor 60 instead determines that the rhythm is a slow suspected non-lethal arrhythmia, microprocessor 60 applies a second change to a scheduled therapy (192) and increases the NID threshold by a second, e.g., greater, amount (194).

After microprocessor 60 increases the NID threshold by either the first or second amount, microprocessor 60 measures subsequent VCLs (196) to determine whether the increased NID threshold is met (198). If the increased NID threshold is not met, microprocessor 60 resets the NID threshold and the scheduled therapy to their original values. However, if the increased NID threshold is met, microprocessor 60 controls delivery of the scheduled therapy as previously changed based on the determination of whether the suspected non-lethal arrhythmia was a slow suspected non-lethal arrhythmia (202).

Microprocessor 60 can apply either a first or second change to the scheduled therapy based on the determination of whether the suspected non-lethal arrhythmia is a slow suspected non-lethal arrhythmia in a number of ways. For example, where microprocessor 60 would reduce the number of defibrillation or cardioversion shocks and add ATP attempts for suspected non-lethal arrhythmias, microprocessor 60 can eliminate the shocks and instead control delivery of ATP alone for slow suspected non-lethal arrhythmias. In some embodiments, microprocessor 60 can simply cancel delivery of any therapy upon the determination that a suspected non-lethal arrhythmia is a slow suspected non-lethal arrhythmia. In such embodiments, microprocessor 60 can detect the arrhythmia when the increased NID threshold is met and not control delivery of any therapy in response to the detection, or can simply reset the NID threshold upon the determination that the suspected non-lethal arrhythmia is a slow suspected non-lethal arrhythmia.

Figure 10:
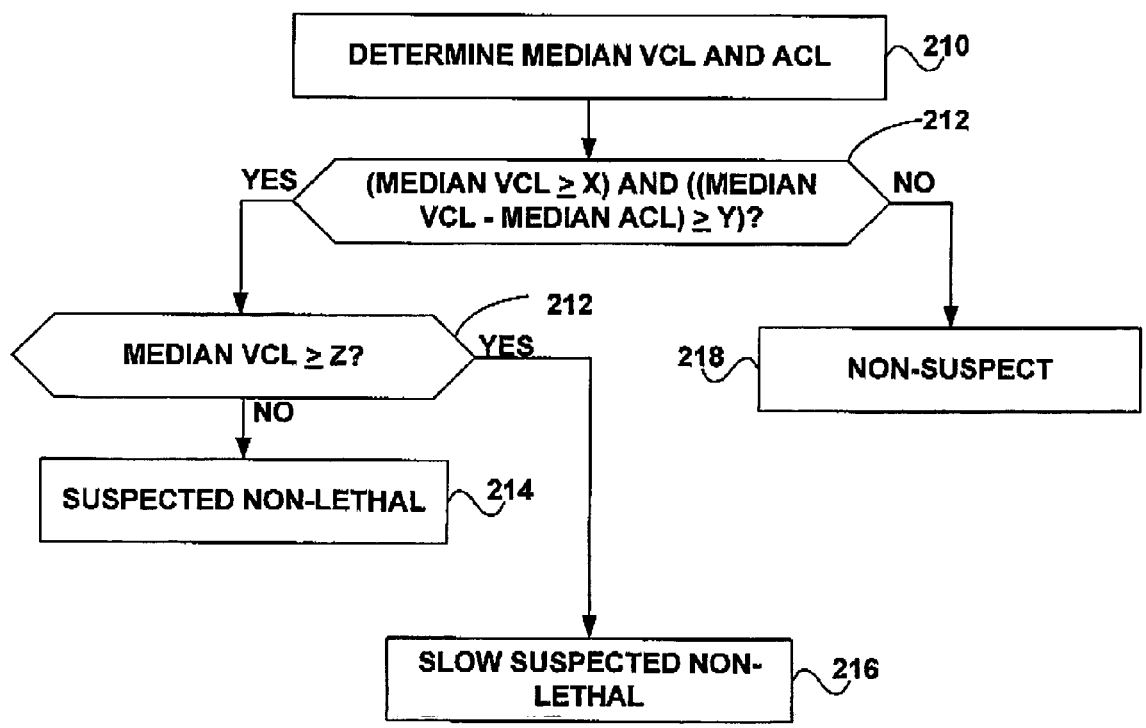
FIG. 10 is a flow diagram illustrating an example technique employed by the implantable medical device of FIG. 1 to determine whether a suspected non-lethal arrhythmia is a slow suspected non-lethal arrhythmia.

FIG. 10 is a flow diagram illustrating an example technique employed by IMD 10 to determine whether a suspected non-lethal arrhythmia is a slow suspected non-lethal arrhythmia. In particular, FIG. 10 illustrates an example technique employed by IMD 10 to determine whether a ventricular rhythm is a suspected SVT, and further determine whether the suspected SVT is a slow SVT.

IMD 10 determines the median VCL and ACL for a number of previous intervals, e.g., the twelve intervals that preceded the interval in which a NID for an arrhythmia is met (210). If the median VCL is greater than or equal to a minimum VCL threshold ("X") for suspected non-lethal arrhythmias, and the difference between the median VCL and median ACL is greater than or equal to a suspect threshold ("Y") (212), microprocessor 60 further determines whether the median VCL is greater than or equal to a slow suspected non-lethal arrhythmia threshold ("Z"). Microprocessor 60 classifies the rhythm as one of a suspected non-lethal arrhythmia and a slow a suspected non-lethal arrhythmia based on this determination (214, 216). On the other hand, if either of minimum VCL ("X") and suspect ("Y") thresholds is not met, microprocessor 60 determines that the rhythm is non-suspect, and proceeds to deliver a ventricular therapy scheduled for the detected arrhythmia (218).

As described above with reference to FIG. 7, RAM 62 stores the threshold values, and in exemplary embodiments the minimum VCL threshold ("X") is approximately 270 milliseconds while the suspect threshold ("Y") is equal to −30 milliseconds. Further, in exemplary embodiments, the slow suspected non-lethal arrhythmia threshold ("Z") is approximately 370 milliseconds. Moreover, as described above, in some embodiments IMD 10 determines whether the rhythm is a suspected non-lethal arrhythmia by determining whether the rhythm is a monomorphic VT instead of or in addition to determining that a ventricular arrhythmia is a suspected SVT. Threshold values for monomorphic VT classification can be the same as an SVT threshold values, e.g., 270 and 370 milliseconds, or can be slightly longer, e.g., 300 and 400 milliseconds.

Various embodiments of the invention have been described. However, one skilled in the art will appreciate that various modifications can be made to the described embodiments without departing from the scope of the invention. For example, although described herein as applied to detection and treatment of ventricular arrhythmias, the therapy delaying and changing techniques of the invention can be additionally or alternatively applied by IMDs when detecting and treating atrial arrhythmias. These and other embodiments are within the scope of the following claims.

The invention claimed is:

1. A method of determining a status of a ventricular rhythm of a heart using an implantable medical device comprising a sensing electrode, a therapy electrode and a processor, comprising the steps of:
   measuring a ventricular cycle length of a ventricular rhythm of a heart detected by said sensing electrode;
   comparing with the processor a number of times the ventricular cycle length exceeds a ventricular cycle length threshold against a predetermined number of intervals to detect threshold (NID threshold) to obtain a comparison; then
   determining, with the processor and based on the comparison, if the ventricular rhythm is a lethal arrhythmia or a non-lethal arrhythmia; and then
   if the ventricular rhythm is a lethal arrhythmia, delivering a therapy to the heart using the therapy electrode;
   if the ventricular rhythm is a non-lethal arrhythmia, withholding the therapy to the heart and increasing the NID threshold; then
   measuring a subsequent ventricular cycle length of the ventricular rhythm of the heart detected by said sensing electrode;
   comparing with the processor an updated number of times the ventricular cycle length and the subsequent ventricular cycle length exceed the ventricular cycle length threshold against the NID threshold, as updated, to obtain an update of the comparison, the updated number of times additively incorporating an instance of the subsequent ventricular cycle length exceeding the ventricular cycle length threshold; then
   returning to the determining step; and
   wherein the NID threshold is reset to the predetermined NID threshold by the processor upon a first predetermined condition and the number of times the ventricular cycle length exceeds a ventricular cycle length threshold is reset upon a second predetermined condition.

2. The method of claim 1, wherein the ventricular rhythm comprises one of ventricular fibrillation, ventricular tachycardia, and fast ventricular tachycardia, and the NID threshold comprises one of a ventricular fibrillation NID threshold, a ventricular tachycardia NID threshold, a fast ventricular tachycardia NID threshold, and a combined count NID threshold.

3. The method of claim 1, wherein the determining step comprises determining that the ventricular rhythm is non-lethal if the ventricular rhythm is one of a suspected supraventricular tachycardia and a monomorphic ventricular tachycardia.

4. The method of claim 1, wherein the comparison step comprises making a comparison of the ventricular cycle length to an atrial cycle length, wherein the ventricular cycle length is one of a median ventricular cycle length and a mean ventricular cycle length and the atrial cycle length is one of a median atrial cycle length and a mean atrial cycle length; and
   wherein the determining step comprises determining whether the ventricular rhythm is a non-lethal arrhythmia based on the comparison of the ventricular cycle length.

5. The method of claim 4, wherein the determining whether the ventricular rhythm step comprises determining whether the ventricular rhythm is non-lethal if the ventricular cycle length is greater than or substantially equal to the atrial cycle length.

6. The method of claim 5, wherein the determining whether the ventricular rhythm is non-lethal step comprises comparing a difference between the ventricular cycle length and the atrial cycle length to a suspect threshold value.

7. The method of claim 4, wherein increasing the NID threshold comprises selecting an amount by which the NID threshold is increased based on the comparison of the ventricular cycle length and the atrial cycle length.

8. The method of claim 1, wherein increasing the NID threshold comprises selecting an amount by which the NID threshold is increased based on one of a median ventricular cycle length and a mean ventricular cycle length.

9. The method of claim 1, wherein the determining step comprises determining whether the ventricular rhythm is the non-lethal arrhythmia if the ventricular cycle length exceeds a minimum ventricular cycle length threshold, and the ventricular cycle length is one of a median ventricular cycle length and a mean ventricular cycle length.

10. The method of claim 1, wherein the determining step is further based on determining whether the ventricular rhythm is a non-lethal arrhythmia based on analyzing at least one of regularity of a plurality of ventricular cycle lengths, regularity of a morphological feature of the ventricular rhythm, A-V association, and rate of onset of at least one of atrial cycle lengths, ventricular cycle lengths, and A-V interval lengths.

11. The method of claim 1, wherein the determining step is further based on determining whether the ventricular rhythm is a non-lethal arrhythmia based on analyzing one of an intracardiac pressure, respiration, and an activity level of a patient.

12. The method of claim 1, wherein increasing the NID threshold comprises increasing the NID threshold to a first value, the method further comprising:
   determining if the ventricular rhythm is a slow non-lethal arrhythmia; and
   increasing the NID threshold to a second value based on the slow non-lethal arrhythmia.

13. The method of claim 12, wherein determining whether the ventricular rhythm is a slow non-lethal arrhythmia comprises determining whether one of a median ventricular cycle length and a mean ventricular cycle length is greater than or equal to a threshold value.

14. The method of claim 1, further comprising after the comparing step, identifying at least one of cardiac and non-cardiac oversensing, and further comprising, after the identifying step, determining whether the ventricular rhythm is a non-lethal arrhythmia based on the identifying step.

15. The method of claim 14, wherein identifying at least one of cardiac and non-cardiac oversensing comprises determining whether one of a median ventricular cycle length and a mean ventricular cycle length is less than or equal to an oversensing threshold value.

16. The method of claim 1, wherein the therapy comprises delivering a withheld scheduled therapy only if the withheld scheduled therapy has been previously withheld.

17. The method of claim 16, wherein the withheld scheduled therapy is obtained by applying a first change to a scheduled therapy, the method further comprising:
   determining whether the ventricular rhythm is a slow non-lethal arrhythmia; and
   then
   applying a second change to the therapy based on the slow non-lethal arrhythmia.

18. The method of claim 1, wherein increasing the NID threshold comprises increasing the NID threshold by a first amount based upon a first determination that the ventricular rhythm is a non-lethal arrhythmia, and wherein a subsequent increasing the NID threshold comprises increasing the NID threshold by a second amount based upon a second determination that the ventricular rhythm is a non-lethal arrhythmia.

19. The method of claim 1, wherein a clinician programs the predetermined NID threshold and an amount by which the NID threshold is increased in the increasing the NID threshold step.

20. An implantable medical device for a patient having a heart which generates a ventricular rhythm, comprising:
a sensing electrode sensitive to the ventricular rhythm;
a therapy electrode configured to deliver a therapy to the heart;
a processor, operatively coupled to the sensing electrode and the therapy electrode, configured to:
measure a ventricular cycle length of the ventricular rhythm;
compare a number of times the ventricular cycle length exceeds a ventricular cycle length threshold against a predetermined number of intervals to detect threshold (NID threshold) to obtain a comparison; then perform a determine operation, based on the comparison, comprising determining if the ventricular rhythm is a lethal arrhythmia or a non-lethal arrhythmia; and then
if a lethal arrhythmia, deliver a therapy to the heart with the therapy electrode;
if a non-lethal arrhythmia, withhold the therapy to the heart and increase the NID threshold; then
measure a subsequent ventricular cycle length of the ventricular rhythm of the heart;
compare an updated number of times the ventricular cycle length and the subsequent ventricular cycle length exceed the ventricular cycle length threshold against the NID threshold, as updated, to obtain an update of the comparison, the updated number of times additively incorporating an instance of the subsequent ventricular cycle length that exceeds the ventricular cycle length threshold; then
return to the determine operation; and
wherein the processor resets the NID threshold to the predetermined NID threshold upon a first predetermined condition and the number of times the ventricular cycle length exceeds a ventricular cycle length threshold is reset upon a second predetermined condition.

21. The device of claim 20, wherein the ventricular rhythm comprises one of ventricular fibrillation, ventricular tachycardia, and fast ventricular tachycardia, and the NID threshold comprises one of a ventricular fibrillation NID threshold, a ventricular tachycardia NID threshold, a fast ventricular tachycardia NID threshold, and a combined count NID threshold.

22. The device of claim 20, wherein the determine operation determines that the ventricular rhythm is non-lethal if the ventricular rhythm is one of a suspected supraventricular tachycardia and a monomorphic ventricular tachycardia.

23. The device of claim 20, wherein the determine operation determines that the ventricular rhythm is a non-lethal rhythm by comparing a ventricular cycle length to an atrial cycle length and determining whether the ventricular rhythm is a non-lethal arrhythmia based on the comparison, and wherein the ventricular cycle length is one of a median cycle length and the atrial cycle length is one of the median cycle length and the mean cycle length.

24. The device of claim 23, wherein the determine operation determines that ventricular cycle length is greater than or substantially equal to the atrial cycle length.

25. The device of claim 24, wherein the determine operation determines that the ventricular cycle length is greater than or substantially equal to the ventricular cycle length by comparing a difference between the ventricular cycle length and the atrial cycle length to a suspect threshold value.

26. The device of claim 23, wherein the processor selects an amount by which the NID threshold is increased based on the comparison of the ventricular cycle length and the atrial cycle length.

27. The device of claim 23, wherein the processor selects an amount by which the NID threshold is increased based on one of a median ventricular cycle length and a mean ventricular cycle length.

28. The device of claim 20,
wherein the determine operation determines that a ventricular cycle length exceeds a minimum ventricular cycle length threshold, and determines that the ventricular rhythm is a non-lethal arrhythmia based on the determination that the ventricular cycle length exceeds a minimum ventricular cycle length threshold; and
wherein the ventricular cycle length is one of a median ventricular cycle length and a mean ventricular cycle length.

29. The device of claim 20, wherein the determine operation is further based on determining if the ventricular rhythm is a non-lethal arrhythmia by analyzing at least one of the regularity of a plurality of ventricular cycle lengths, regularity of a morphological feature of the ventricular rhythm, A-V association, and rate of onset of at least one of atrial cycle lengths, ventricular cycle lengths, and A-V interval lengths.

30. The device of claim 20, further comprising a pressure sensor implanted within the patient to detect an intracardiac pressure, wherein the processor further determines that the ventricular rhythm is a non-lethal arrhythmia based on the intracardiac pressure.

31. The device of claim 20, further comprising a circuit to measure an intrathoracic impedance of a patient via the sensing electrode, wherein the determines operation determines that the ventricular rhythm is a non-lethal arrhythmia based on the intrathoracic impedance.

32. The device of claim 20, further comprising an activity sensor to detect a patient activity of the patient, and further comprising a determines operation further determines that the ventricular rhythm is a non-lethal arrhythmia based on the patient activity.

33. The device of claim 20, wherein increasing the NID threshold comprises increasing the NID threshold to a first value based upon a first determination that the ventricular rhythm is a slow non-lethal arrhythmia, and increasing the NID threshold to a second value based upon a second determination that the ventricular rhythm is a slow non-lethal arrhythmia.

34. The device of claim 33, wherein the determine operation determines that the ventricular rhythm is a slow non-lethal arrhythmia based on a determination that one of a median ventricular cycle length and a mean ventricular cycle length is greater than or equal to a ventricular cycle length threshold value.

35. The device of claim 20, wherein the determine operation determines that the ventricular rhythm is a non-lethal arrhythmia by identifying at least one of cardiac oversensing and non-cardiac oversensing.

36. The device of claim 35, wherein the determine operation identifies at least one of cardiac oversensing and non-cardiac oversensing by determining whether one of a median ventricular cycle length and a mean ventricular cycle length is less than or equal to an oversensing threshold value.

37. The device of claim 20, wherein the therapy is a withheld scheduled therapy only if the withheld scheduled therapy has been previously withheld.

38. The device of claim 37, wherein in response to the determine operation determining that the ventricular rhythm is a non-lethal arrhythmia the withheld scheduled therapy is changed by applying a first change to a scheduled therapy, determining that the ventricular rhythm is a slow non-lethal arrhythmia, and applying a second change to the scheduled therapy based on the determination of a slow non-lethal arrhythmia.

39. The device of claim 20, wherein the processor increases the NID threshold by a first amount based upon a first determination that the ventricular rhythm is a non-lethal arrhythmia, and increases the NID threshold by a second amount based upon a second determination that the ventricular rhythm is a non-lethal arrhythmia.

40. The device of claim 20, wherein a clinician programs the predetermined NID threshold and an amount by which the NID threshold is increased when the processor increases the NID threshold.

41. The device of claim 20, wherein the device is implantable within a patient.

42. The device of claim 20, wherein the device comprises one of a pacemaker and a pacemaker-cardiovertor-defibrillator.

43. An implantable medical device for determining a status of a ventricular rhythm of a heart, comprising:
means for measuring a ventricular cycle length of a ventricular rhythm of a heart;
means for comparing a number of times the ventricular cycle length exceeds a ventricular cycle length threshold against a predetermined number of intervals to detect threshold (NID threshold) to obtain a comparison;
means for determining, based on the comparison, if the ventricular rhythm is a lethal arrhythmia or a non-lethal arrhythmia;
means for delivering a therapy to the heart if the ventricular rhythm is a lethal arrhythmia,;
means for withholding the therapy to the heart and increasing the NID threshold if the ventricular rhythm is a non-lethal arrhythmia;
means for measuring a subsequent ventricular cycle length of the ventricular rhythm of the heart;
means for comparing an updated number of times the ventricular cycle length and the subsequent ventricular cycle length exceed the ventricular cycle length threshold against the NID threshold, as updated, to obtain an update of the comparison, the updated number of times additively incorporating an instance of the subsequent ventricular cycle length that exceeds the ventricular cycle length threshold;
means for returning to the means for determining; and
wherein the NID threshold is reset to the predetermined NID threshold upon a first predetermined condition and the number of times the ventricular cycle length exceeds a ventricular cycle length threshold is reset upon a second predetermined condition.

44. The device of claim 43, wherein the means for determining comprises at least one of means for determining whether the ventricular rhythm is a suspected supraventricular tachycardia and means for determining whether the ventricular rhythm is a monomorphic ventricular tachycardia.

45. The device of claim 43, wherein the means for determining comprises means for comparing a ventricular cycle length to an atrial cycle length, wherein the ventricular cycle length is one of a median ventricular cycle length and a mean ventricular cycle length and the atrial cycle length is one of a median atrial cycle length and a mean atrial cycle length.

46. The device of claim 43, wherein the means for determining is further based on means for determining the ventricular rhythm is the non-lethal arrhythmia based on analyzing at least one of regularity of a plurality of ventricular cycle lengths, regularity of a morphological feature of the ventricular rhythm, A-V association, and rate of onset of at least one of atrial cycle lengths, ventricular cycle lengths, and A-V interval lengths.

47. The device of claim 43, further comprising means for detecting an intracardiac pressure, wherein the means for determining is further based on means for determining if the ventricular rhythm is a non-lethal arrhythmia based on an analysis of the intracardiac pressure.

48. The device of claim 43, further comprising means for measuring an intrathoracic impedance of a patient, wherein means for determining comprises means for determining whether the ventricular rhythm is a non-lethal arrhythmia based on an analysis of the intrathoracic impedance.

49. The device of claim 43, further comprising means for detecting activity of a patient, and further comprising means for determining whether the ventricular rhythm is a non-lethal arrhythmia based on an analysis of the activity of the patient.

50. The device of claim 43, wherein the means for determining comprises means for identifying at least one of cardiac and non-cardiac oversensing.

51. The device of claim 50, wherein means for identifying at least one of cardiac and non-cardiac oversensing comprises means for determining whether one of a median ventricular cycle length and a mean ventricular cycle length is less than or equal to an oversensing threshold value.

* * * * *